(12) United States Patent
Schwartz

(10) Patent No.: US 6,994,094 B2
(45) Date of Patent: Feb. 7, 2006

(54) METHOD AND DEVICE FOR TRANSSEPTAL FACILITATION BASED ON INJURY PATTERNS

(75) Inventor: Yitzhack Schwartz, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 156 days.

(21) Appl. No.: 10/425,165

(22) Filed: Apr. 29, 2003

(65) Prior Publication Data
US 2004/0220462 A1    Nov. 4, 2004

(51) Int. Cl.
A61B 19/00    (2006.01)
A61B 5/04    (2006.01)

(52) U.S. Cl. .................. 128/898; 128/899; 600/374
(58) Field of Classification Search .............. 600/374, 600/381; 128/898, 899
See application file for complete search history.

(56) References Cited

U.S. PATENT DOCUMENTS

| 5,391,199 | A | 2/1995 | Ben-Haim |
| 5,462,545 | A | 10/1995 | Wang et al. |
| 6,285,898 | B1 * | 9/2001 | Ben-Haim .................. 600/374 |
| 6,332,089 | B1 | 12/2001 | Acker et al. |
| 6,484,118 | B1 | 11/2002 | Govari |
| 6,814,733 | B2 * | 11/2004 | Schwartz et al. ............. 606/41 |
| 2002/0017445 | A1 | 2/2002 | Mukai |
| 2004/0082860 | A1 | 4/2004 | Haissaguerre |
| 2004/0133113 | A1 * | 7/2004 | Krishnan .................... 600/508 |

FOREIGN PATENT DOCUMENTS

| WO | WO 96/05768 A1 | 2/1996 |
| WO | WO 99/39624 A1 | 8/1999 |
| WO | WO 02/071955 A2 | 9/2002 |

OTHER PUBLICATIONS

European Patent Application No. EP04252449 dated Aug. 25, 2004.
Bidoggia et al. Transseptal Left Heart Catherization: Usefulness of the Intracavitary Electrocardiogram in the Localization of the Fossa Ovalis, *Catherization and Cardiovascular Diagnosis* 24(3) :221-225(1991).

* cited by examiner

*Primary Examiner*—Lee S. Cohen
(74) *Attorney, Agent, or Firm*—Louis J. Capezzuto

(57) ABSTRACT

A method for performing a procedure at the fossa ovalis in the septal wall of the heart includes the steps of providing a sheath having a body wherein the body has a lumen extending therethrough and an open end at the distal end of the body. The body also has at least one electrode and a position sensor at the distal end of the body. The position sensor generates signals indicative of the location of the distal end of the body. The sheath is navigated to the septal wall using the position sensor and the fossa ovalis in the septal wall is identified using the at least one electrode of the sheath.

19 Claims, 17 Drawing Sheets

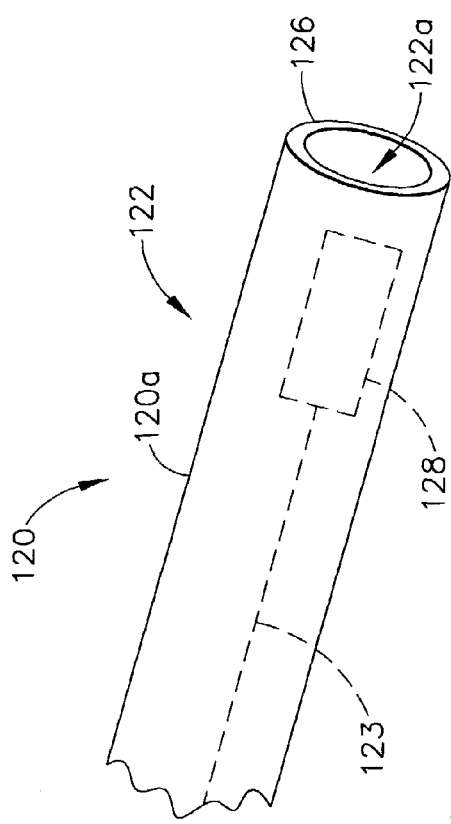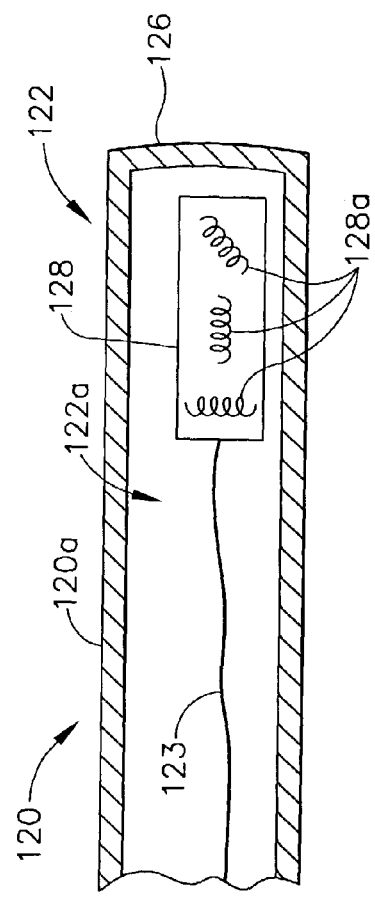
FIG. 4A
FIG. 4B

METHOD AND DEVICE FOR TRANSSEPTAL FACILITATION BASED ON INJURY PATTERNS

FIELD OF INVENTION

The present invention relates to methods and devices for facilitating diagnostic and therapeutic procedures on tissue and more particularly, relates to methods and devices for performing a transseptal facilitation procedure.

BACKGROUND OF THE INVENTION

In medical procedures involving a patient's heart 100, there are numerous diagnostic and therapeutic procedures that require transseptal left heart catheterization, i.e. catherization through left atrium 110 as shown in FIG. 1. The transseptal approach is an essential maneuver that provides access for both interventional cardiologists who perform antegrade mitral balloon valvuloplasty and for cardiac electrophysiologists who ablate left sided accessory pathways or perform transcatheter atrial-fibrillation therapeutic tactics.

In 15–25% of the normal healthy population, the interarterial septum (IAS) 105 has fossa ovalis or foramen ovale 107 that is patent, i.e. patent foramen ovale (PFO). The PFO is one of the three obligatory shunts in the normal fetal intrauterine blood circulation. The incidental presence of a PFO often enables a swift passage of a guide-wire across right atrium 115 and through septum 105. Pediatric cardiologists often use this route.

For procedures involving patient's already having a PFO (pre-existing hole at the fossa ovalis 107), generally a transesophageal ultrasonic probe (not shown) is inserted into the patient's mouth and placed in the esophagus. In most cases, the transesophageal ultrasonic probe is positioned approximately 30–35 cm from the mouth, i.e. in most cases positioned just above the patient's stomach.

Under transesophageal echocardiography (TEE), i.e. transesophageal ultrasonic guidance, a wire (not shown) is inserted into the right atrium 115 through an appropriate vessel such as the inferior vena cava 108 wherein the wire is guided through the fossa ovalis 107 by gently lifting the tissue flap away from the patent opening of the IAS 105 at the fossa ovalis 107. Once the wire is inserted through the fossa ovalis 107, the wire is guided to one of the pulmonary veins 116 for placement of the distal end of the wire in order to properly position and anchor the wire in the opening of the pulmonary vein 116. Accordingly, the pulmonary vein 116 has been proven to be a very reliable and steady anchoring point for the wire.

Once the wire is properly positioned in the fossa ovalis 107 and anchored in the pulmonary vein 116, a catheter sheath ("over-the-wire" type) is guided over the wire through the right atrium 115 and the fossa ovalis 107 and positioned within the left atrium 110, for instance, very close to the opening of the pulmonary vein 116.

Once the catheter sheath has been properly positioned, the wire is removed from the patient's heart 100 and other therapeutic and/or diagnostic devices are delivered through the catheter sheath. Some of these devices include implantable devices such as implantable pacemakers, electrodes, atrial septal defect (ASD) occlusion devices, etc. Accordingly, the implantable device is deliverable with typical delivery devices such as the Amplatzer® Delivery System, manufactured by AGA Medical Corporation of Golden Valley, Minn.

After placement of the catheter sheath, the implantable device is deployed from the catheter sheath within the fossa ovalis 107. Upon deployment, the implantable device is implanted into the IAS 105 thereby occluding the opening (PFO) at the fossa ovalis 107.

In all other patients, a transseptal perforation technique (anterograde approach) is necessary. However, this procedure can result in various life-threatening complications, some of which may occur because of insufficient antaomical landmarks in the heart 100. Thus, several methods have been proposed for guidance of transseptal catheterization, including transesophageal echocardiography (TEE) and intracardiac echo (ICE).

When conducting an anterograde approach with TEE, a transesophageal ultrasonic probe is positioned in the patient's esophagus as described above. Under transesophageal ultrasonic imaging guidance, an opening is made in the IAS 105 at the fossa ovalis 107 in order to facilitate and accommodate another therapeutic and/or diagnostic device. Thus, the opening is made with a penetrating device having a penetrating member such as a standard needle catheter, for example, the BRK™ Series Transseptal Needle manufactured by St. Jude Medical, Inc. of St. Paul, Minn. Accordingly, under transesophageal ultrasonic guidance, the needle catheter is initially placed in the right atrium 115 and positioned at the fossa ovalis 107. At this point, the tip of the needle of the needle catheter penetrates the fossa ovalis 107 and the catheter is inserted through the fossa ovalis 107 into the left atrium 110 through the newly created opening in the fossa ovalis 107 by the needle catheter. Once the opening in the fossa ovalis 107 is created, other therapeutic and/or diagnostic devices can be utilized.

Performing transseptal perforation safely and effectively during an anterograde approach procedure requires considerable expertise and only a minority of currently practicing physicians are performing this type of procedure on a regular, routine basis. In fact, many electrophysiologists are refraining from performing transseptal procedures because of lack of skill and unavailable guidance.

Up till now, there have been no devices or methods that can allow a physician to efficiently perform a transseptal facilitation or perforation procedure in an effective manner.

SUMMARY OF THE INVENTION

The present invention is directed toward methods and devices for performing diagnostic and/or therapeutic procedures on tissue and organs. Although the methods and their devices in accordance with the present invention can be used for any type of medical procedure (therapeutic and/or diagnostic procedure), the present invention is more specifically directed toward methods for performing a transseptal facilitation procedure on the septal wall of the heart. Particularly, the methods and devices in accordance with the present invention are useful for accurately identifying the location of the fossa ovalis and for facilitating the penetration of the septal wall at the fossa ovalis with a penetrating device (penetrating member) especially for those procedures involving an anterograde approach.

One embodiment of the present invention is a method for performing a procedure at the fossa ovalis in the septal wall of the heart wherein the method comprises the steps of providing a sheath comprising a body wherein the body has a lumen extending therethrough and an open end at a distal end of the body. The body also has at least one electrode at the distal end of the body for sensing parameters or characteristics of the tissue (septal wall of the heart in one example). One type of characteristic measured with the at least one electrode of the sheath body are injury patterns formed in or exhibited by the tissue. When identifying the fossa ovalis in the septal wall, the at least one electrode of the sheath is used to identify the fossa ovalis based on particular characteristics of the tissue of the septum and the fossa ovalis, for example, based on injury patterns exhibited by both the septum and the fossa ovalis.

Another aspect of the present invention is a device useful for performing a procedure on tissue, for instance, a transseptal facilitation procedure. One embodiment of the device in accordance with the present invention comprises a body having a lumen extending therethrough and an open end at a distal end of the body. At least one electrode is located at the distal end of the body for determining an injury pattern on the tissue.

Another embodiment of the present invention is directed toward a method for performing a procedure at the fossa ovalis in the septal wall of the heart wherein the method comprises the steps of providing a sheath comprising a body wherein the body has a lumen extending therethrough and an open end at a distal end of the body. The body also has at least one electrode and a position sensor at the distal end of the body. The position sensor generates signals indicative of the location of the distal end of the body. The sheath is navigated to the septal wall using the position sensor. And, the fossa ovalis in the septal wall is identified using the at least one electrode of the sheath.

The present invention also comprises a device for performing a procedure on tissue, for example, a transseptal facilitation procedure, wherein the device comprises a body having a lumen extending therethrough and an open end at a distal end of the body. The body also includes at least one electrode at the distal end for determining an injury pattern on the tissue. The body also includes a position sensor at the distal end for generating signals indicative of a location of the distal end of the body.

Another alternative embodiment in accordance with the present invention is directed toward a method for performing a procedure at the fossa ovalis in the septal wall of a heart wherein the method comprises the steps of identifying the septal wall of the heart and identifying the fossa ovalis in the septal wall. A point is identified on the fossa ovalis and the point is then tagged at the fossa ovalis. A sheath comprising a body wherein the body has a lumen extending therethrough and an open end at a distal end of the body is also used. The body also includes a position sensor at the distal end of the body wherein the position sensor generates signals indicative of a location of the distal end of the body. The sheath is navigated to the fossa ovalis at the tagged point using the position sensor. In one example, the tagged point is a location coordinate (having position and orientation coordinates) displayed on a map such as an electroanatomical map. In another example in accordance with the present invention, the tagged point is a physical tag, such as an active tag or a passive tag, which is placed at the point (at the identified location, i.e. position and/or orientation coordinates), at the fossa ovalis of the septal wall.

In all embodiments of the method in accordance with the present invention that involve a transseptal facilitation procedure, once the fossa ovalis is identified in the septal wall, a penetrating device (penetrating member) is used within the lumen of the sheath body and is extended out of the distal end of the sheath body such that the distal tip of the penetrating member punctures or penetrates the fossa ovalis creating an apperture in the fossa ovalis leading to the left atrium of the heart. Accordingly, access to the left atrium of the heart is provided.

These and other objects, features and advantages of the present invention will be more readily apparent from the detailed description set forth below, taken in conjunction with the accompanying drawings.

BRIEF DESCRIPTION OF THE DRAWINGS

FIG. 4A is a partial perspective view of a distal end of a first alternative embodiment of the sheath of FIG. 2 in accordance with the present invention;

FIG. 4B is a partial view in cross-section of the sheath of FIG. 4A in accordance with the present invention;

DESCRIPTION OF THE PREFERRED EMBODIMENTS

The present invention is directed toward methods and devices for performing diagnostic and/or therapeutic procedures on tissue to include, more particularly, procedures used to identify particular tissue, such as the fossa ovalis of the septal wall of the heart as part of a transseptal facilitation procedure.

As used herein, the term "tissue" is meant to describe all solid or semi-solid cellular matter in the body, such as muscle, nerve, connective tissue, vasculature and bone. Blood and other liquid matter, such as lymph, interstitial fluids or other fluids in the body, are excluded from the definition of "tissue" as defined herein.

Figure 1:
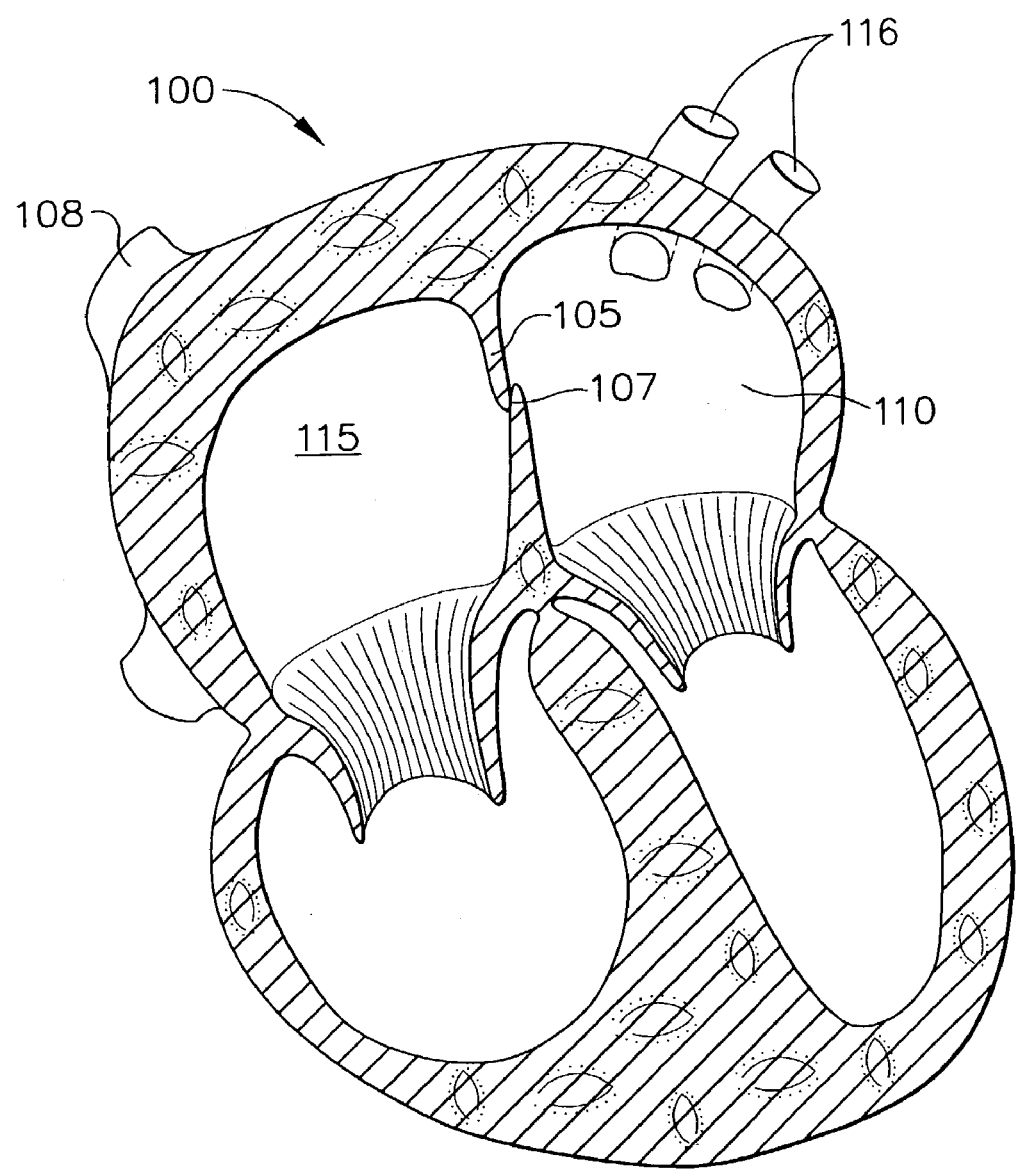
FIG. 1 is a schematic view in cross-section of a heart.
Figure 2:
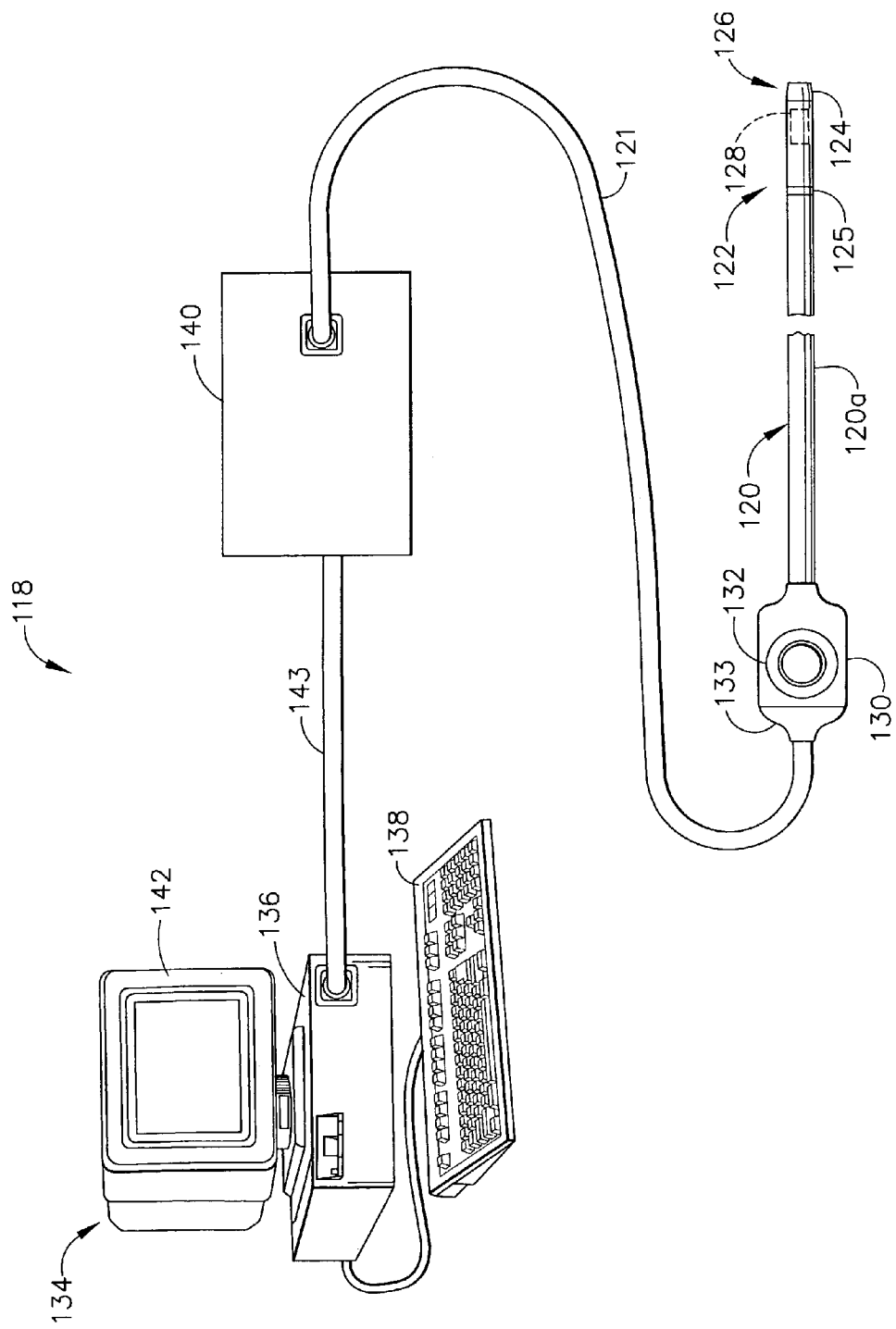
FIG. 2 is a schematic view of a location system with a guiding sheath having a position sensor in accordance with the present invention.

One embodiment of the present invention, included within a diagnostic mapping and therapeutic delivery system, generally designated 118, is best shown in FIG. 2. The system comprises a flexible guiding sheath 120 for insertion into the human body (patient 90 shown in FIG. 3) by physician 151, and preferably, into a chamber, for example right atrium 115, of the human heart 100 (FIG. 1). The sheath 120 includes a sheath body 120a having a distal end 22 and defining a lumen extending longitudinally through the body 120a and terminating in an opening 122a at distal tip 126. The lumen and opening 122a of the sheath body 120a serve as a working channel as will be described in greater detail later in this disclosure. The distal end 122 includes a distal tip electrode arrangement 124 (which is a recording electrode arrangement) at distal tip 126 for recording and measuring the electrical properties of the heart tissue such as recording injury patterns. Electrode arrangement 124 is also useful for sending electrical signals to the heart 100 for diagnostic purposes, e.g., for pace mapping, and/or for therapeutic purposes, e.g., for ablating defective cardiac tissue. While electrode 124 is designed to be in contact with tissue when performing its functions of receiving electrical signals from and transmitting electrical signals to the heart, it should be understood that electrode 124 is not always in contact with tissue. For example, electrode 124 may not be in contact with tissue as it is being advanced through the vasculature to the heart 100, or when it is being directed from one point to another point within the heart chamber such as right atrium 115.

Distal end 122 of sheath 120 may optionally include a second electrode 125 such as a reference electrode 125 for providing an internal reference measurement of impedance while the reference electrode 125 is in contact with blood but is not in contact with tissue or when both electrode 124 and second electrode 125 are in contact with tissue. Distal end 122 of sheath 120 further includes a location sensor (also referred to as a position sensor) 128 in some embodiments according to the present invention, that generates signals used to determine the position and orientation coordinates (location information) of the distal end 122 of sheath 120 within the patient's body 90. Location sensor 128 is preferably adjacent to distal tip 126 of sheath 120. There is preferably a fixed positional and orientational relationship of location sensor 128, tip 126 and electrode arrangement 124. Wires 123 carry the relevant signals to and from electrode 124, electrode 125 (if utilized) and location sensor 128.

The location sensor (position sensor) 128 is used to sense the instantaneous position of the distal end 122 and distal tip 126 of sheath 120. In a preferred embodiment of the invention, location sensor 128 is an AC magnetic field receiver, which senses an AC magnetic field generated by a plurality of magnetic field transmitters 127 which are also referred to as magnetic field generators or radiators which generate AC magnetic fields respectively to define a fixed frame of reference. Preferred location sensors 128 are further described in U.S. Pat. No. 5,391,199 and in PCT application PCT/US95/01103, published as WO96/05768 (U.S. patent application Ser. No. 08/793,371 filed May 14, 1997), the disclosures of which are incorporated herein by reference. The position and orientation coordinates of the distal end 122 and distal tip 126 of the sheath 120 are ascertained by determining the position and orientation of the location sensor 128 (through identifying the position and orientation coordinates thereof). In one embodiment of the invention, the location sensor 128 comprises one or more antennas 128a (FIGS. 4B and 6B), for example one or more coils, or a plurality of coils 128a which are irradiated by two or three radiators (transmitters) 127 which are outside the body surface of the patient 90. It should be understood that placement of the transmitters 127, as well as their size and shape, will vary according to the application of the invention. Preferably the transmitters 127 useful in a medical application comprise wound annular coils from about 2 to 20 cm in outer diameter (O.D.) and from about 0.5 to 2 cm thick, in a coplanar, triangular arrangement where the centers of the coils are from about 2 to 30 cm apart. Bar-shaped transmitters or even triangular or square-shaped coils could also be useful for such medical applications. Moreover, in instances where a prone patient 90 will be the subject of a procedure involving the instant invention, the transmitters 127 are preferably positioned in or below the surface upon which the patient 90 is resting (such as operating table 131), substantially directly below the portion of the patient's body 90 where a procedure is being performed. In other applications, the transmitters 127 may be fairly close to the skin of the patient 90. The transmitters 127 are driven by a radiator driver preferably in a manner described below, and the signals received by the receiving antennas (coils) 128a of the location sensor 128 are amplified and processed, together with a representation of the signals used to drive transmitters 127, preferably in the manner described below, in signal processor 140, to provide a display or other indication of the position and orientation of the distal end 122 on monitor or display 142 of console 134. Transmitters 127 may be arranged in any convenient position and orientation, so long as they are fixed in respect to some reference frame, and so long as the transmitters 127 are non-overlapping, that is, there are no two transmitters 127 with the exact, identical location, i.e. position and orientation. When driven by radiator driver, the transmitters 127 generate a multiplicity of distinguishable AC magnetic fields that form the magnetic field sensed by receiving antennas (coils)128a in the location sensor 128. The magnetic fields are distinguishable with regard to the frequency, phase, or both frequency and phase of the signals in the respective magnetic fields. Time multiplexing is also possible. Location sensor 128 may consist of a single coil 128a, but preferably includes two or more and more preferably three sensor coils 128a wound on either air cores or a core of material. In a preferred embodiment of the invention the coils 128a have mutually orthogonal axes, one of which is conveniently aligned with the long longitudinal axis of the guiding sheath 120. Unlike prior art position sensors (used for other applications) which contain three coils that are concentrically located, or at least whose axes intercept, the coils 128a of the preferred embodiment of the invention are closely spaced along the longitudinal axis of the sheath 120 to reduce the diameter of the location sensor 128 and thus make the sensor 128 suitable for incorporation into the sheath 120 (thereby defining a lumen 122a as a working channel within guiding sheath 120). For most aspects of the present invention, quantitative measurement of the position and orientation (by determining position coordinates and orientation coordinates) of the sheath distal end 122 and distal tip 126 relative to a reference frame is necessary. This fixed frame of reference requires at least two non-overlapping transmitters 127 that generate at least two distinguishable AC magnetic fields; and location sensor 128, consisting of at least two non-parallel coils 128a to measure the magnetic field flux resulting from the at least two distinguishable magnetic fields. The number of transmitters 127 times the number of coils 128a is equal to or greater than the number of degrees of freedom of the desired quantitative measurement of the position and orientation of the coils 128a of location sensor 128 relative to the reference frame established by the fixed or stationary transmitters 127, i.e. fixed to underside of table 131. Since, in a preferred embodiment of the invention it is preferred to determine six position and orientation coordinates (X, Y, Z directions and pitch, yaw and roll orientations) of the distal end 122 and distal tip 126 of the sheath 120, at least two coils 128a are required in the location sensor 128. Preferably three coils 128a are used to improve the accuracy and reliability of the position measurement. In some applications where fewer dimensions are required, only a single coil 128a may be necessary for the location sensor 128 such that when used with transmitters 127, the system 118 determines five position and orientation coordinates (X, Y, Z directions and pitch and yaw orientations). Specific features and functions of a single coil system, (also referred to as a single axis system) is described in commonly assigned U.S. Pat. No. 6,484,118, which is incorporated herein in its entirety by reference. Leads (wires) 123 are used to carry signals detected by the sensor coils 128a to signal processor 140, via the proximal end of the sheath 120, for processing to generate the required position and orientation information. Preferably, leads 123 are twisted pairs to reduce pick-up and may be further electrically shielded. In one embodiment of the invention, coils 128a have an inner diameter of 0.5 mm and have 800 turns of 16 micrometer diameter to give an overall coil diameter of 1–1.2 mm. The effective capture area of the coil 128a is preferably about 400 mm$^2$. It will be understood that these dimensions may vary over a considerable range and are only representative of a preferred range of dimensions. In particular, the size of the coils 128a can be as small as 0.3 mm (with some loss of sensitivity) and as large as 2 or more mm. The wire size of the coils 128a can range from 10–31 micrometers and the number of turns between 300 and 2600, depending on the maximum allowable size and the wire diameter. The effective capture area should be made as large as feasible, consistent with the overally size requirements. While the preferred sensor coil shape 128a is cylindrical, other shapes can also be used. For example a barrel shaped coil can have more turns than a cylindrical shaped coil for the same diameter of catheter. Also, square or other shaped coils may be useful depending on the geometry of the sheath 120. Location sensor 128 is preferably used to determine when sheath 120, is both in contact with the tissue of heart 100 (FIG. 1) and also to determine when the heart 100 is not in motion. During diastole, the heart 100 is relatively motionless for a short period of time (at most, a few hundred milliseconds). Alternatively to using a location sensor 128, the location of sheath 120 is determined using outside sensing or imaging means.

Guiding sheath 120 is either an over-the-wire type sheath that utilizes a guide wire (not shown) or may include a detachably connected handle 130, which includes controls 132 to steer the distal end 122 of the sheath 120 in a desired direction, such as deflecting the distal end 122, or to position and/or orient distal end 122 or distal tip 126 as desired.

Figure 3:
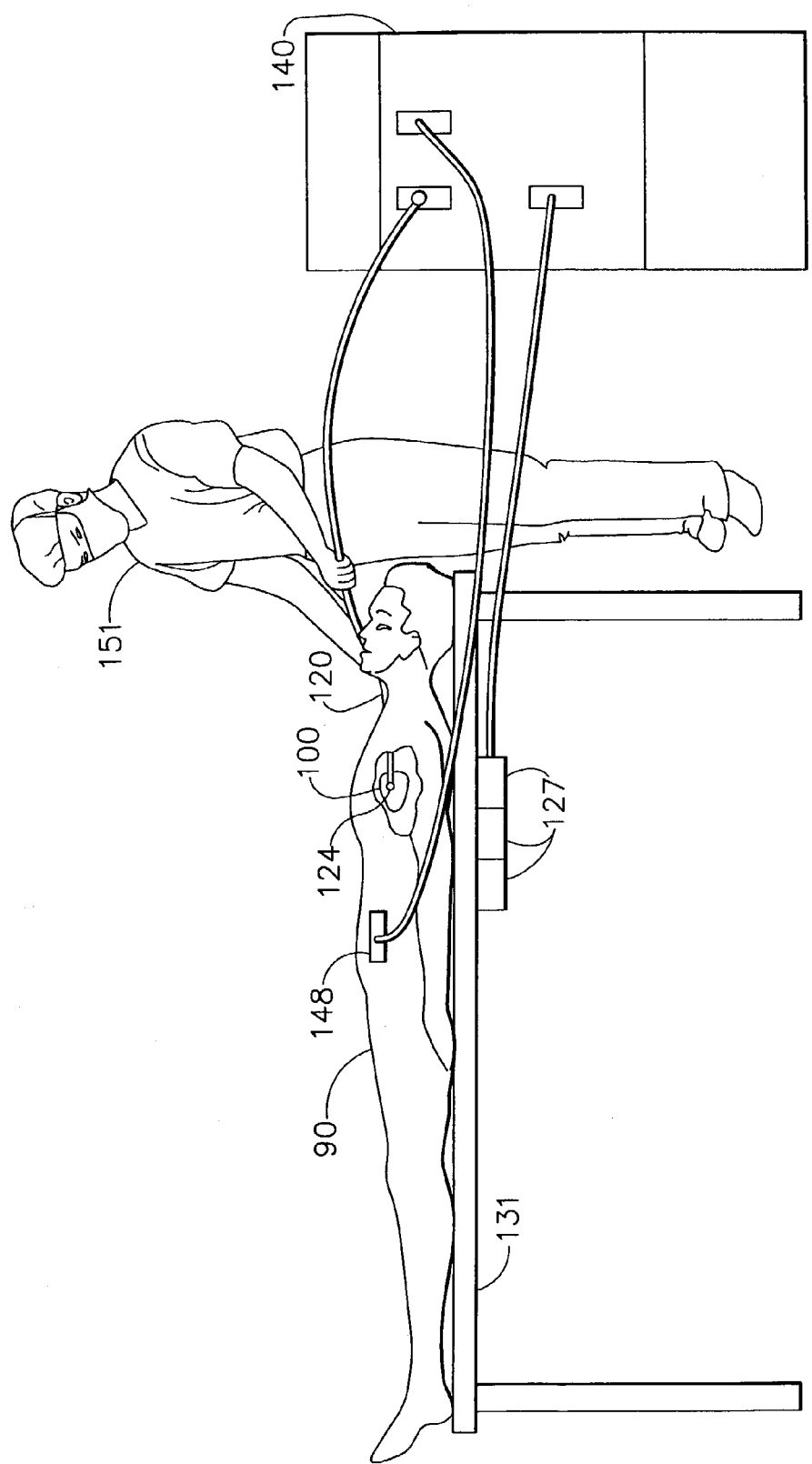
FIG. 3 is a schematic view of the system of FIG. 2 in use on a patient in accordance with the present invention.

The system 118, as shown in FIGS. 2 and 3, further comprises a console 134, which enables the user (physician 151) to observe and regulate the functions of sheath 120. Console 134 preferably includes a computer 136, keyboard 138, and display 142. Computer 136 contains control circuits to permit control and operation of the system 118 and to start and stop the collection of data from the sheath's electrode arrangement 124, second electrode or reference electrode 125 and from location sensor 128. Computer 136 further uses the electrical and or mechanical and location information acquired by electrodes 124 and 125 (when utilized) and location sensor 128 carried through wires 123 and processed by the circuits of signal processor 140 in the reconstruction and visualization of a map such as an electrical or electromechanical map of a portion of the heart 100 such as a chamber wall or interatrial septum (IAS) 105.

Signal processor 140 has circuits which typically receive, amplify, filter and digitize signals from sheath 120, including signals generated by location sensor 128, tip electrode 124 and second or reference electrode 125 (when utilized). Circuits of signal processor 140 further compute the position and orientation (position coordinates and orientation coordinates) of the sheath 120 as well as the electrical characteristics of the portions of heart 100 from the signals generated by location sensor 128 and tip electrode 124 respectively. Circuits of signal processor 140 also process body surface electrocardiogram signals. The digitized signals generated by the circuits of signal processor 140 are received and used by computer 136 to reconstruct and visualize an electrical or electromechanical map of portions of the heart 100 to include the septum 105.

In some embodiments of the invention, a return electrode 148 is used, for instance, by placement on an outer surface of the patient's body 90 and is preferably relatively large to provide low impedance between the return electrode 148 and the patient's body 90. For example, Electrosurgical Patient Plate model 1149F, supplied by 3M of St. Paul, Minn., which has an area of approximately 130 cm$^2$, may be satisfactorily used as the return electrode 148 in the system and method of the invention.

Figure 6A:
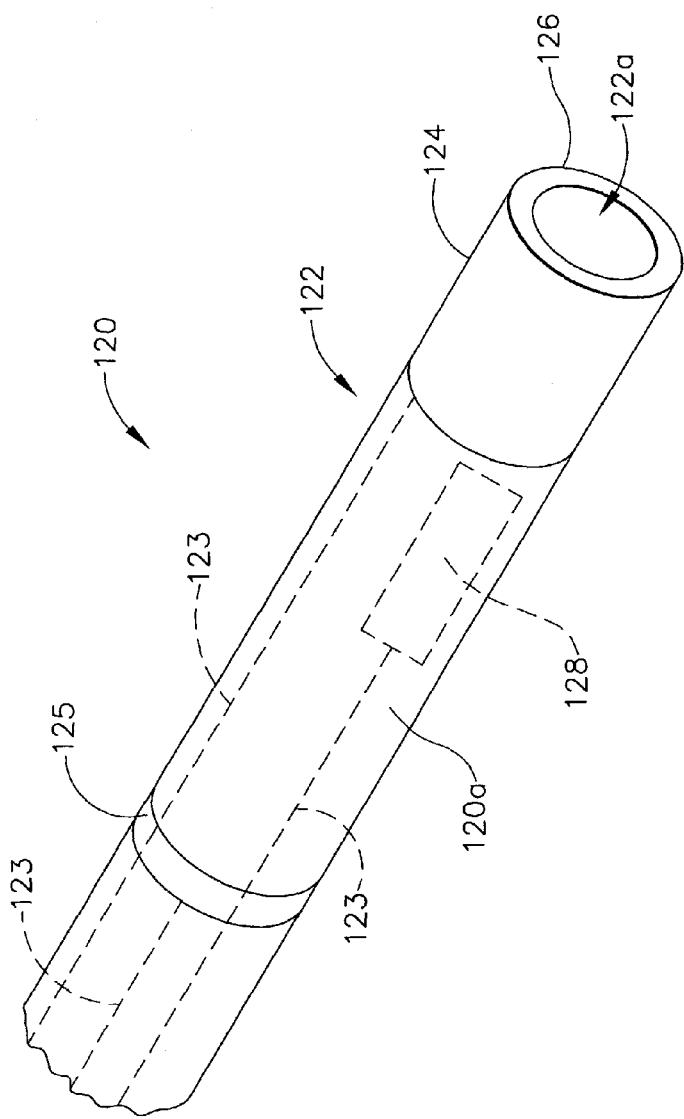
FIG. 6A is a partial perspective view of a distal end of the sheath of FIG. 2 in accordance with the present invention.
Figure 6B:
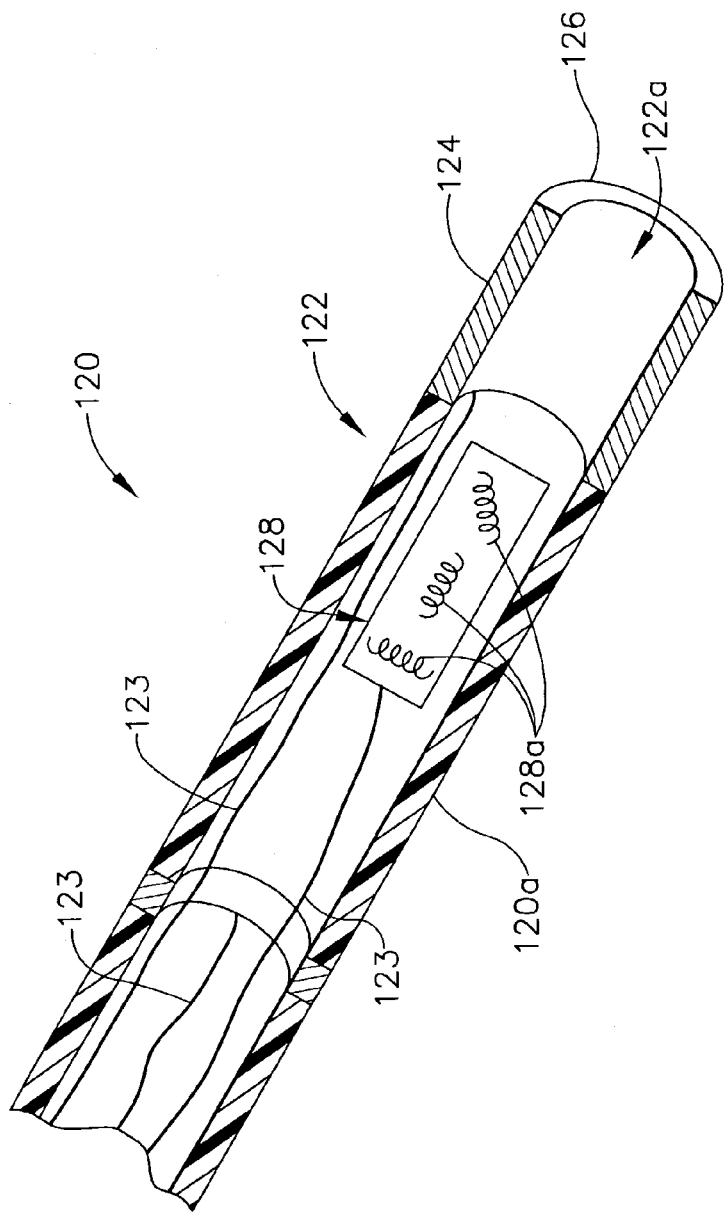
FIG. 6B is a partial view in cross-section of the sheath of FIG. 6A in accordance with the present invention.

FIGS. 6A and 6B depict the guiding sheath 120 used in conjunction with the location system 118 (FIG. 2). As shown in FIGS. 6A and 6B, the first electrode 124 is a distal tip electrode located at the distal end 122, particularly at the distal tip 126, of the body 120a of the sheath 120. In this embodiment in accordance with the present invention, the distal tip electrode 124 can take the form of any desired shape or configuration, for example, a single elongated segment or a single electrode circumferentially arranged around the distal tip 126 of the body 120a as shown. The location sensor 128 is located proximal to the tip electrode 124 and is located within the lumen 122a of the sheath body 120a. In this embodiment in accordance with the present invention, the location sensor 128 has a plurality of sensor coils 128a, for instance, three coils 128a (FIG. 6B). However, as mentioned above, the location sensor 128 can comprise any number of coils 128a such as a single coil 128a (as part of a single axis sensor), two coils 128a or three coils, etc. The location sensor 128 is attached to the sheath body 120*a* at a location proximal the tip electrode 124 in a manner that does not obstruct the lumen 122*a* of the sheath body 120*a*.

Accordingly, the lumen 122*a* defines a working channel that facilitates the introduction of secondary devices such as a penetrating device 150 having a penetrating member or any other desired diagnostic and/or therapeutic device configured in a manner, i.e. having a smaller diameter than the diameter defined by the lumen 122*a* to facilitate diagnostic and/or therapeutic procedures using the guiding sheath 120, such as procedures as the novel transseptal facilitation procedures in accordance with the present invention described in greater detail later in this disclosure.

Figure 5:
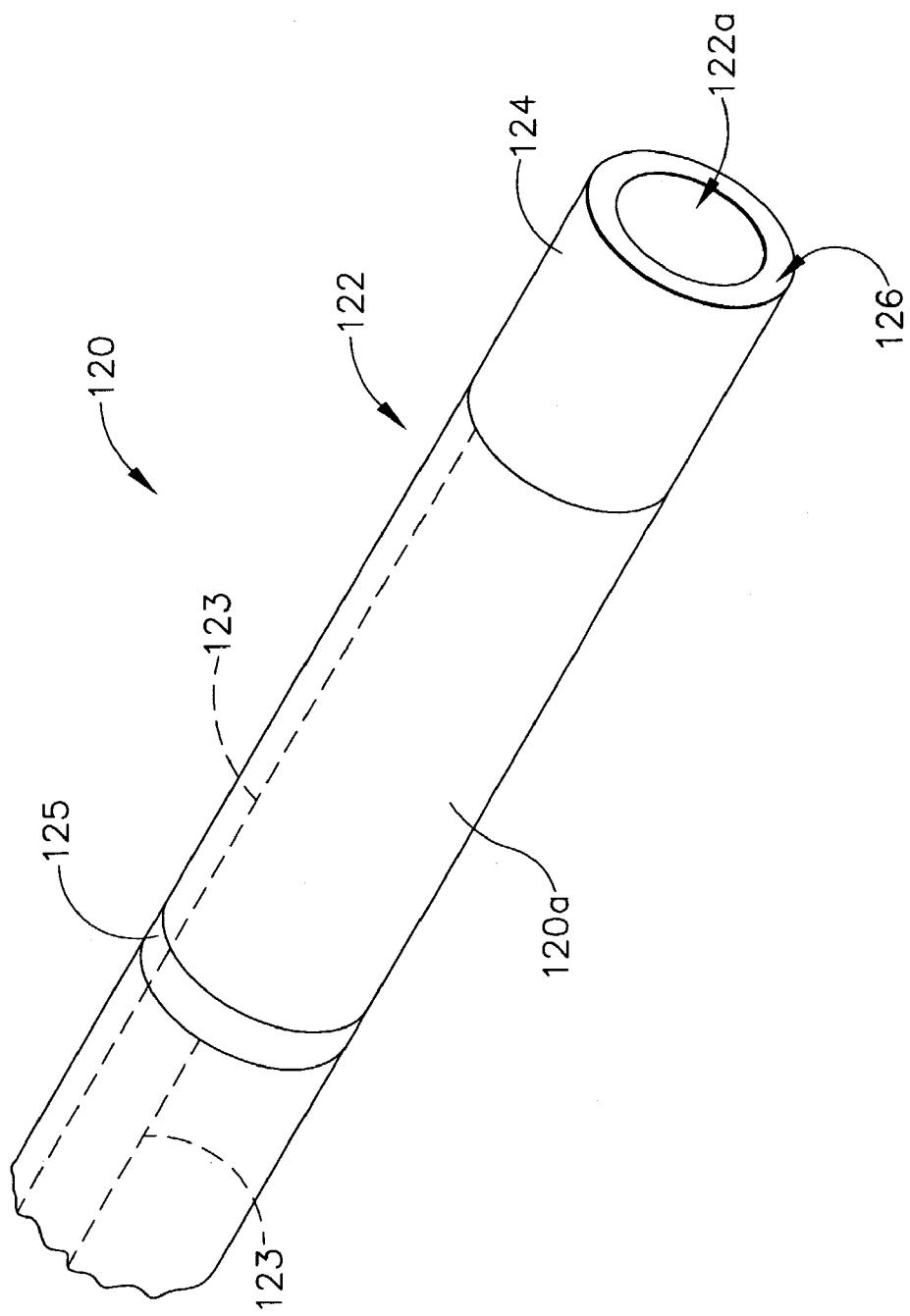
FIG. 5 is a partial perspective view of a distal end of a second alternative embodiment of the sheath of FIG. 2.

An alternative embodiment of the guiding sheath 120 is shown in FIG. 5 and consists of a single tip electrode 124 circumferentially arranged around the distal end 122 (at the distal tip 126) of the sheath body 120*a*. In this emodiment, the guiding sheath 120 does not have a location sensor. Accordingly, the sheath 120 of FIG. 5 can be used in conjunction with other imaging and/or location modalities which can include fluoroscopic devices, and echography devices, ultrasound visualization devices such as transesophageal echocardiography and intracardiac echo devices or any other desired imaging modality. Particular methods of the present invention utilizing the guiding sheath 120 of FIG. 5 will be addressed later in this disclosure.

Moreover, although the guiding sheath 120 depicted in FIG. 5 is shown as a single tip electrode 124 circumferentially arranged around the distal end 122 of the body 120*a* at the distal tip 126, the single electrode 124 can be any desired shape or configuration such as an elongated segment electrode, etc.

Figure 7:
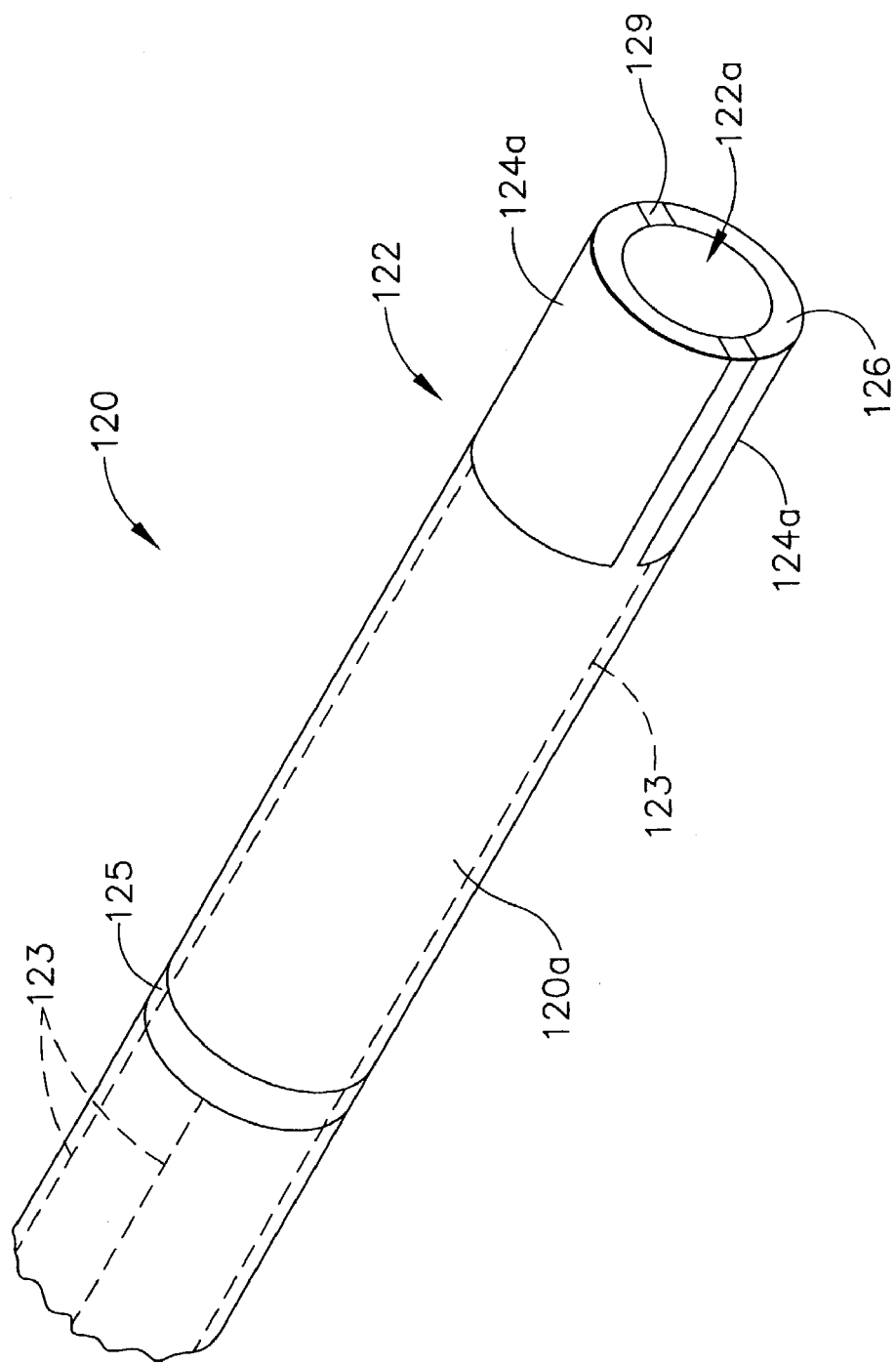
FIG. 7 is a partial perspective view of a distal end of a third alternative embodiment of the sheath of FIG. 2 in accordance with the present invention.

FIG. 7 shows another alternative embodiment for the guiding sheath 120 having distal end 122 with a split-tip electrode arrangement. In this embodiment in accordance with the present invention, the split-tip electrode arrangement comprises a hemi-circular arrangement having two electrode segments 124*a* located on different halves of the distal end 122 at the distal tip 126 of the sheath body 120*a*. An insulating portion 129 separates the electrode segments 124*a* and serves as an insulating barrier positioned between each electrode segment 124*a*. The two electrode segments 124*a* can function either as two distinct and separate electrodes or the segments 124*a* can function as a single electrode as desired. Each electrode segment 124*a* forms a hemi-circular element at the distal end 126 thereby defining the distal end opening of the lumen 122*a* of the sheath body 120*a*.

Figure 8:
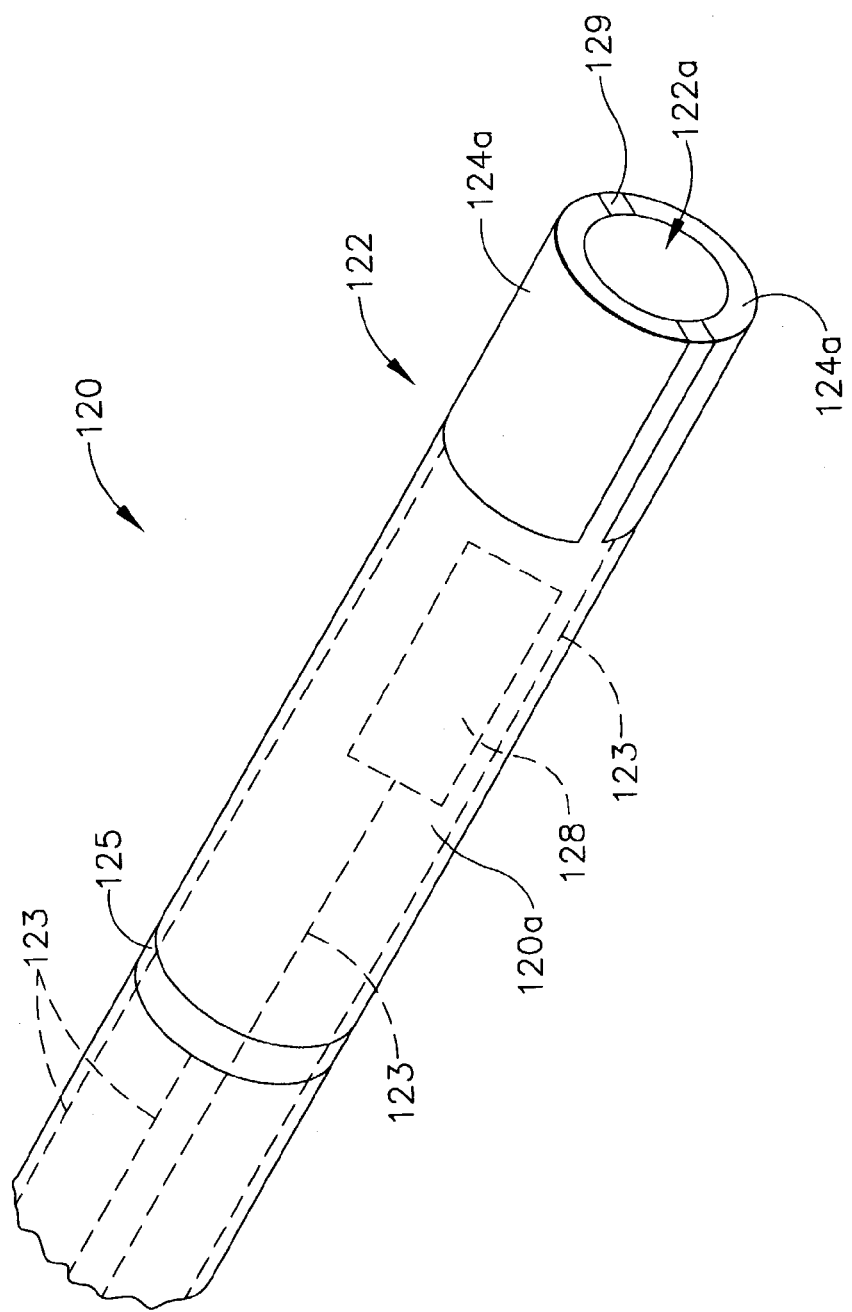
FIG. 8 is a partial perspective view of a distal end of a fourth alternative embodiment of the sheath of FIG. 2 in accordance with the present invention.

FIG. 8 depicts another alternative embodiment of the guiding sheath 120 in accordance with the present invention. The sheath 120*a* of FIG. 8 is similar to the hemi-circular split-tip electrode arrangement shown in FIG. 7 with the addition of location sensor 128 located within the lumen 122*a* of the sheath body 120*a* and attached to inner surface of the body 120*a* defining the lumen 122*a* (working channel) wherein the location sensor 128 is located proximal to the hemi-circular split-tip electrode arrangement 124*a*. The specific components, features and function of the location sensor 128 has been previously described above. Again, the location sensor 128*a* is attached to the inner surface of the sheath body 120*a* thereby defining the lumen 122*a* (working channel) for facilitating and passing of secondary instruments therethrough as described above.

Figure 9:
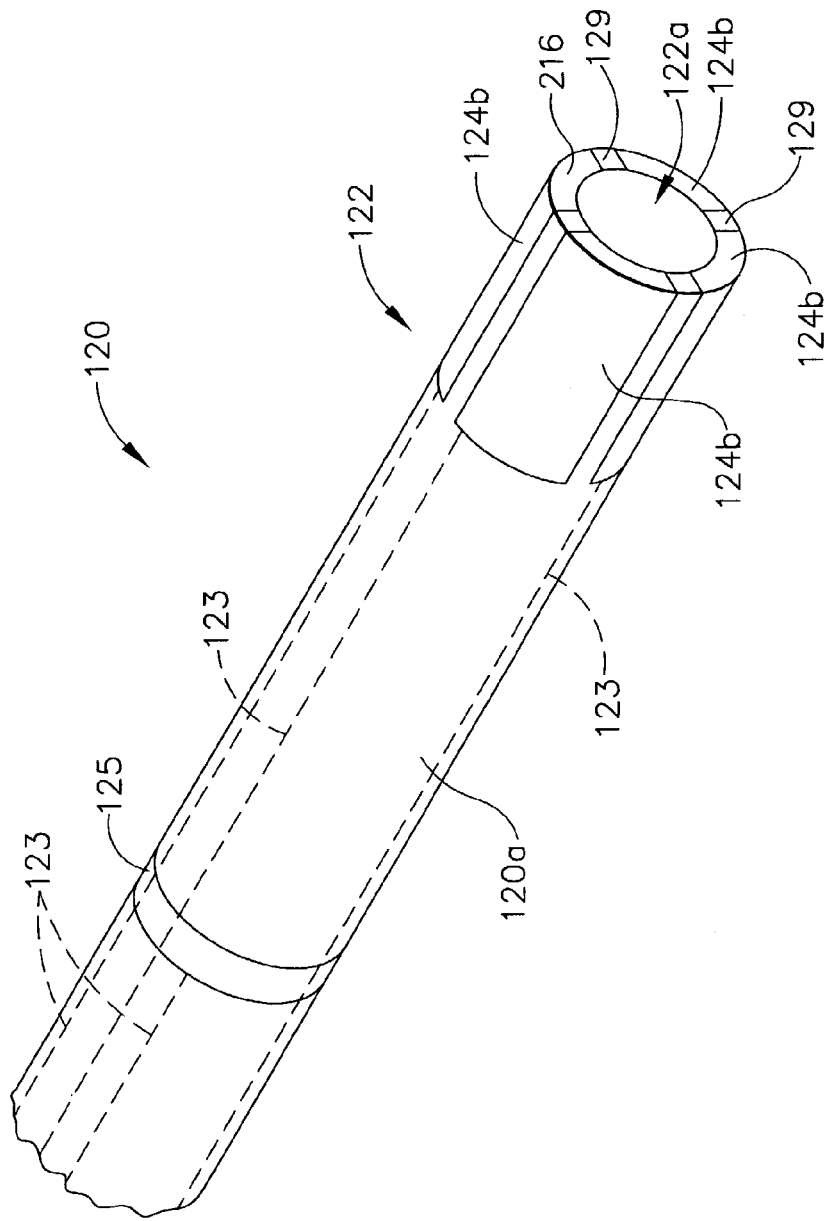
FIG. 9 is a partial perspective view of a distal end of a fifth alternative embodiment of the sheath of FIG. 2 in accordance with the present invention.

FIG. 9 shows another alternative embodiment of the guiding sheath 120 in accordance with the present invention having a semi-circular split-tip electrode arrangement comprising four electrode segments 124*b*. Each electrode segment 124*b* is partially and circumferentially arranged around the circumference of the distal tip 126 of the distal end 122 of the sheath body 120*a*. Each electrode segment 124*b* is separated from an adjacent electrode segment 124*b* by insulating layer 129 which serves as an insulating barrier between adjacent electrode segments 124*b*. The semi-circular split-tip electrode arrangement terminates in a distal opening therein contiguous with the lumen 122*a* for facilitating secondary devices such as those described above for use in methods to be address later in this disclosure.

Additionally, the electrode segments 124*b* can either function as four separate electrodes or four segments of a single electrode (a single distal tip electrode) as desired.

Figure 10:
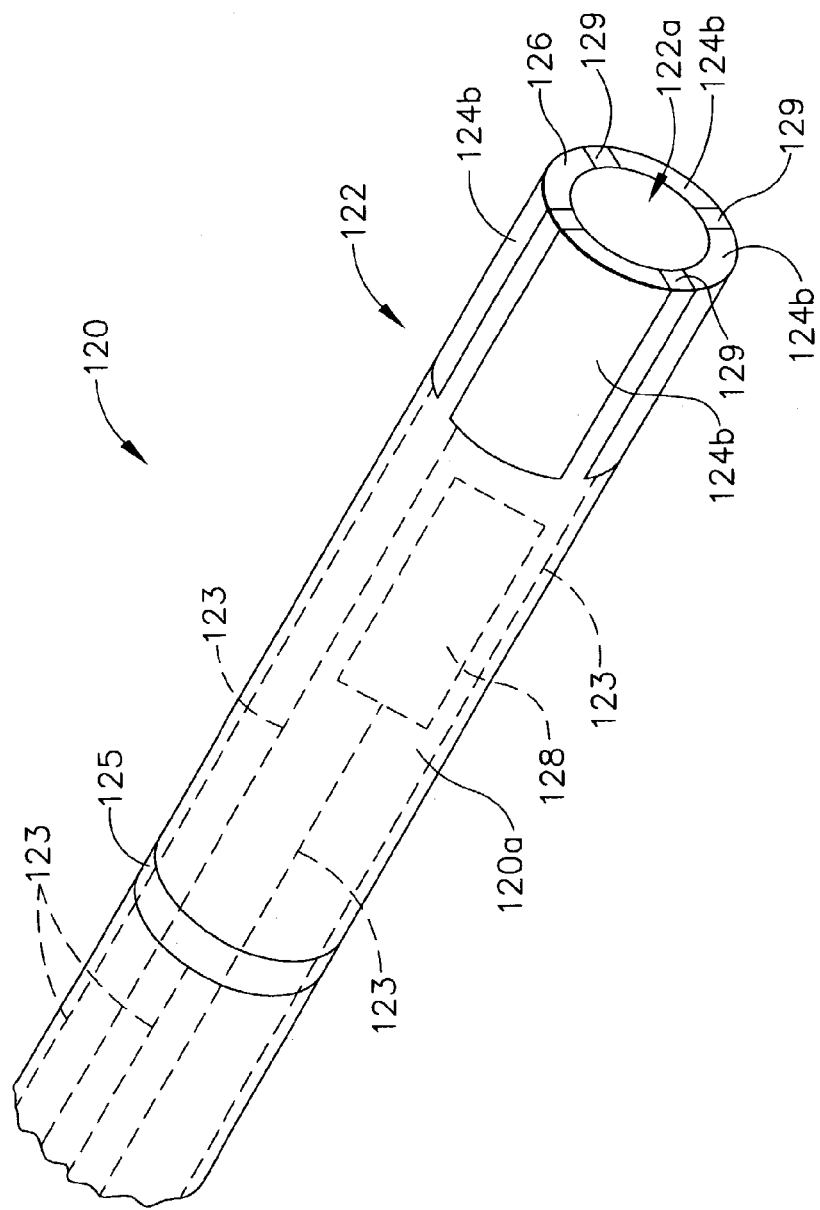
FIG. 10 is a partial perspective view of a distal end of a sixth alternative embodiment of the sheath of FIG. 2 in accordance with the present invention.

FIG. 10 shows another alternative embodiment of the guiding sheath 120 similar to the sheath depicted in FIG. 9 with the addition of the location sensor 128 located within the lumen 122*a* of the sheath body 120*a* and affixed to an inner surface of the sheath body 120*a* and positioned at a location proximal to the electrode segments 124*b*.

Again, the location sensor 128 is affixed to the inner surface of the sheath body 120*a* in a manner that defines the lumen 122*a* as a working channel terminating in an opening at the distal tip 126 of the body 120*a* in order to facilitate the introduction and withdrawal of secondary devices into and out of the sheath body 120*a*.

The alternative embodiments of the guiding sheath 120 depicted respectively in FIGS. 5, 6A, 6B, 7, 8, 9 and 10, all have at least one electrode which functions as a tip-electrode located at the distal tip 126 of the sheath body 120*a*. All of the sheath embodiments in accordance with the present invention have a distal end 122 terminating in a distal tip 126 having a distal end opening contiguous with the lumen 122*a* of the sheath body 120*a* which serves as the working channel for the introduction and withdrawal of secondary devices. Additionally, the alternative distal tip electrode arrangements 124, 124*a* and 124*b* respectively, permit the distal end 122 and distal tip 126 of the guiding sheath 120 to be moved near or over tissue of interest. Particularly, the tip electrode arrangement 124, 124*a* and 124*b* respectively, are used to sense various characteristics or parameters of the tissue and generate signals indicative of these tissue characteristics or tissue parameters which are carried through wires 123 back to the signal processor 140 of the system 118 for measurement, analysis and depiction on the display 142. Although the distal tip electrode arrangements 124, 124*a* and 124*b* respectively used in conjunction with the guiding sheath 120 in accordance with the present invention can be used to detect any type of tissue characteristic or tissue parameter, these alternative distal tip electrode arrangements are particularly useful for sensing and determining injury patterns in tissue. This includes the detection of injury patterns particular to heart tissue to include the intra-arterial septum 105 and the fossa ovalis 107 of the heart 100 in accordance with novel methods of the present invention which will be addressed in greater detail below.

Additionally, the guiding sheath 120 depicted in FIGS. 5, 6A, 6B, 7, 8, 9 and 10 in accordance with the present invention can be used in conjunction with a guide wire, i.e. serve as a guiding sheath or an "over-the-wire" device through use of a guide wire. Alternatively, the guiding sheath 120 of the present invention depicted in FIGS. 5, 6A, 6B, 7, 8, 9 and 10 are not required to be used with a guide wire and can be used without such a device if desired, for example, the guiding sheath 120 can be used with the handle 130 as shown in FIG. 2.

Figure 12A:
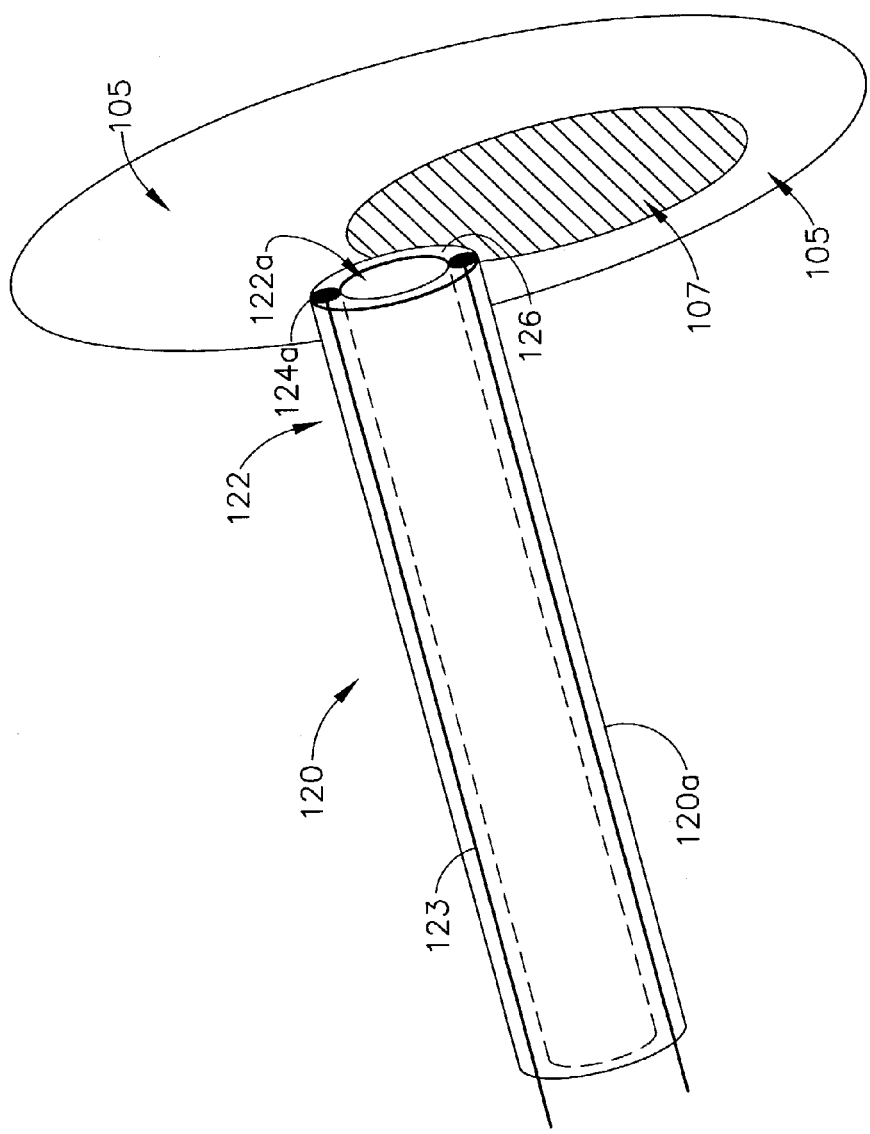
FIG. 12A is a schematic illustration of a guiding sheath having at least one electrode in accordance with the present invention being used for identifying the fossa ovalis in an alternative embodiment of the method in accordance with the present invention.
Figure 12B:
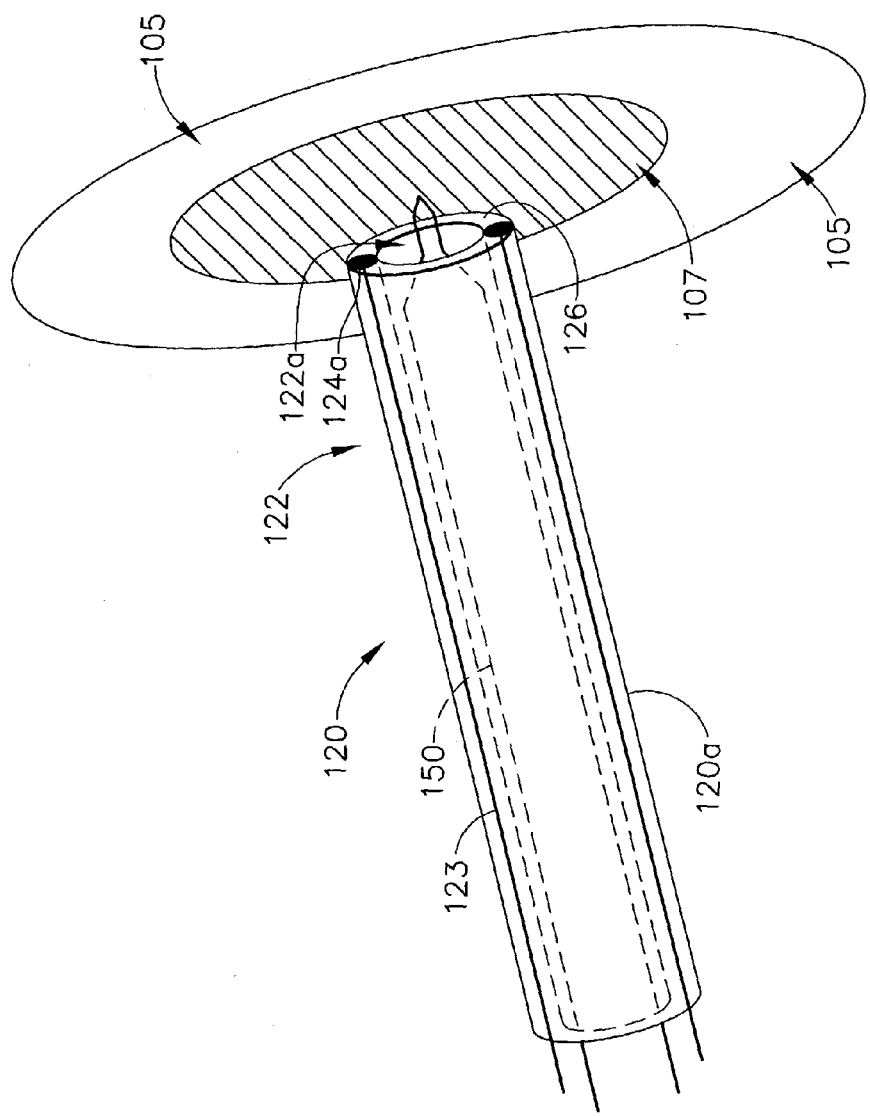
FIG. 12B is a schematic illustration of the sheath having at least one electrode and a penetrating device therein in accordance with the present invention being used to penetrate the fossa ovalis in the method of FIG. 12A in accordance with the present invention.

Although the guiding sheath 120 depicted in FIGS. 5, 6A, 6B, 7, 8, 9 and 10 can be used in any desired tissue or organ sensing procedure, the guiding sheath 120 in accordance with the present invention is particularly useful for a transseptal facilitation procedure. For instance, FIGS. 12A and 12B show the guiding sheath 120 in accordance with the present invention used on the interatrial septum 105 in order to rapidly and efficiently identify the fossa ovalis 107 as well as an appropriate puncture site within the fossa ovalis 107.

In this procedure, the guiding sheath 120 is placed in the patient's body 90 (FIG. 3) and guided into the inferior vena cava 108 and into the right atrium 115. Again, the guiding sheath 120 can be used with or without a guiding wire (not shown). The guiding sheath 120 is guided to the interatrial septum 105 wherein the distal end 122 of the sheath body 120a is used as a probe by placing the distal tip 126 against the tissue, i.e. the septum 105 such that the tip electrode arrangement, i.e. electrode segments 124a contact the tissue of the septum 105. The distal tip electrode segments 124a are used as recording electrodes that record particular characteristics of the septum 105, more particularly, an injury pattern. The injury pattern detected by the recording electrode segments 124a is transmitted through wires 123 back to the signal processor 140 (FIGS. 2 and 3) for analysis.

Injury pattern analysis techniques are described in Bidoggia, et al., Transseptal Left Heart Catheterization: Usefulness of the Intracavitary Electrocardiogram in the Localization of the Fossa Ovalis, *Catheterization and Cardiovascular Diagnosis* 24(3):221–225(1991). When the recording electrode segments are 124a placed against the muscular areas of the septum 105 or the free atrial wall, the recording electrode segments 124a transmit signals that show a marked injury curve and are indicative of an injury pattern. These injury patterns are determined as part of an endoatrial electrocardiogram (EAE) wherein the EAE is depicted on the display 142 (FIG. 2) for analysis by the physician 151 (FIG. 3). The injury patterns depicted in electrocardiogram format are in the form of a PQRST complex that is analyzed in any desired combination of segments or waves. Additionally, when the distal electrode arrangement (recording electrode segments 124a) are pressed into the endocardium at any muscular area of the septum 105 or atrial wall, the injury curve or injury pattern elicited and displayed becomes progressively severe as the pressure in increased against the tissue with the distal tip 126 of the sheath 120. In some instances, higher pressures exerted against this tissue with the distal tip 126 at the distal electrode arrangement results in a PQRST complex that is rather extraordinary or complex, i.e. in some instances it is depicted as a broad and bizarre monophasic injury curve.

Since the muscular areas of the septum 105 or free atrial wall display an injury pattern such as those outlined above, the recording electrode segments 124a of the distal tip electrode arrangement are moved across the septum 105 by moving the electrode segments 124a at distal tip 126 against the tissue of the septum 105 in any desired direction. While moving the distal tip 126 as electrode segments 124a are in contact with the tissue of the septum 105, signals indicative of injury patterns are generated by the distal tip electrode arrangement (electrode segments 124a) and transmitted through wires 123 to signal processor 140 to be recorded and displayed in real time, as a result of the recording electrode segments 124a, which are displayed on the display 142. Since the fossa ovalis 107 has a tissue composition that is significantly thinner tissue (thin membrane when compared to the muscular areas of the septum 105 outside the fossa ovalis 107), the fossa ovalis 107 does not generate the same type of injury pattern exhibited by the muscular areas, i.e. the fossa ovalis 107 exhibits less of an injury pattern than the injury patterns exhibited by the muscular areas (areas outside the fossa ovalis 107) of the septum 105. Additionally, in many instances, the fossa ovalis 107 does not exhibit any injury pattern at all when recording and registering EAE patterns based on PQRST complex and particular segment analysis.

Accordingly, the distal tip electrode arrangement, i.e. in this embodiment recording electrode segments 124a, at the distal tip 126 are navigated along the septum 105 until the recording electrode segments 124a generate signals that exhibit very minor injury patterns (less of an injury pattern), when compared to the injury patterns exhibited by the muscular areas of the septum 105 previously recorded, or no injury patterns at all. Thus, when achieving this level of injury pattern (either slight or nonexistent injury pattern), the physician 151 (FIG. 3) readily knows that he or she has properly identified the fossa ovalis 107.

As shown in FIG. 12B, when the distal tip 126 of distal end 122 of the sheath body 120a is located at the fossa ovalis 107, a secondary device such as a penetrating device 150 having a penetrating member is introduced into the lumen 122a of the sheath body 120a and extended through the opening (122a) in the distal end of the sheath body 120a at the distal tip 126 such that the penetrating member 150 is used to puncture and penetrate the fossa ovalis 107 in order to create an aperture (perforated point in the fossa ovalis 107) with access to the left atrium 110 of the heart 100. In a perforating procedure of the fossal ovalis 107 with the penetrating device 150, the penetrating device 150 is extended through the lumen 122a (working channel) of the sheath body 120a and out of the distal tip 126 at the distal end opening of the body 120a. Once an aperture is made in the fossa ovalis 107 sufficient for accessing the left atrium 110, the penetrating device 150 is withdrawn from the lumen 122a of the sheath body 120a and another secondary device can be inserted into the body 120 through the lumen 122a and extended out of the distal tip 126 of body 120 through the aperture (perforated point) in the fossa ovalis 107) and into the left atrium 110 of the heart 100. Acordingly, this further secondary device enables the physician 151 to perform a diagnostic procedure and/or a therapeutic procedure with this other secondary device in the left atrium 110.

Based on signal differences generated with the distal tip electrode arrangement, i.e. in this embodiment recording electrode segments 124a, the physician 151 (FIG. 3) can determine the exact location of the fossa ovalis 107 by gradually moving the distal end 122 (at the distal tip 126) of the guiding sheath 120 along the septum 105 (with or without an imaging modality such as a fluoroscopy device) while the physician 151 reviews the recorded endocardial signals generated by the recording electrode segments 124a. So long as the distal end 122 of the sheath 120 is relatively stable and one electrode segment 124a records an injury pattern while the second or other electrode segment 124a does not record a similar injury signal or pattern (in the form of a lesser or minor injury pattern than that injury pattern recorded by the first electrode segment 124a), the physician 151 can assume that this second electrode segment 124a is now in contact with or located within the fossa ovalis 107. By moving the distal tip 126 further in the direction of this second electrode segment 124a, i.e. for instance through a slight downward adjustment of the distal end 122 position, both recording electrode segments 124a will then be located within the fossa ovalis 107 such that a transseptal puncture and facilitation procedure such as that described above can be safely performed.

Additionally, it is also easy for the physician 151 to verify when the distal end 122 of the sheath 120 has passed into the left atrium 110, i.e. verification of the sheath 120 into the left atrium 110 after being passed through the newly created aperature in the fossa ovalis 107 of stepum 105. This verification occurs when there is a sudden change exhibited in the P-wave or P-segment recorded by the recording electrode segments 124*a* after the distal end 122 of the sheath 120 has crossed over the septum 105 through the aperture made in the fossa ovalis 107 such that the distal end 122 of the sheath 120 resides within the left atrium 110 of the heart 100.

Figure 13A:
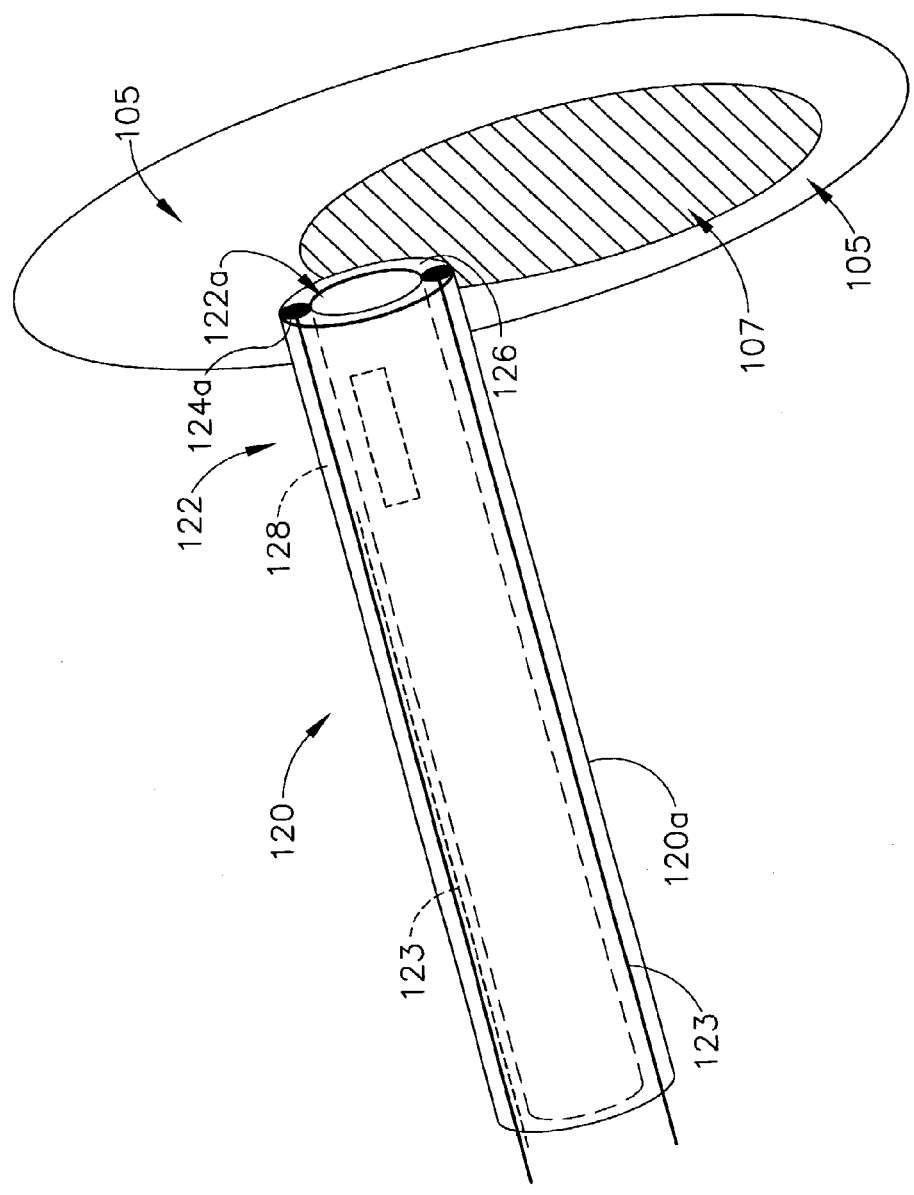
FIG. 13A is a schematic illustration of a guiding sheath having a position sensor and at least one electrode in accordance with the present invention being used to identify the fossa ovalis in another alternative embodiment of the method in accordance with the present invention.
Figure 13B:
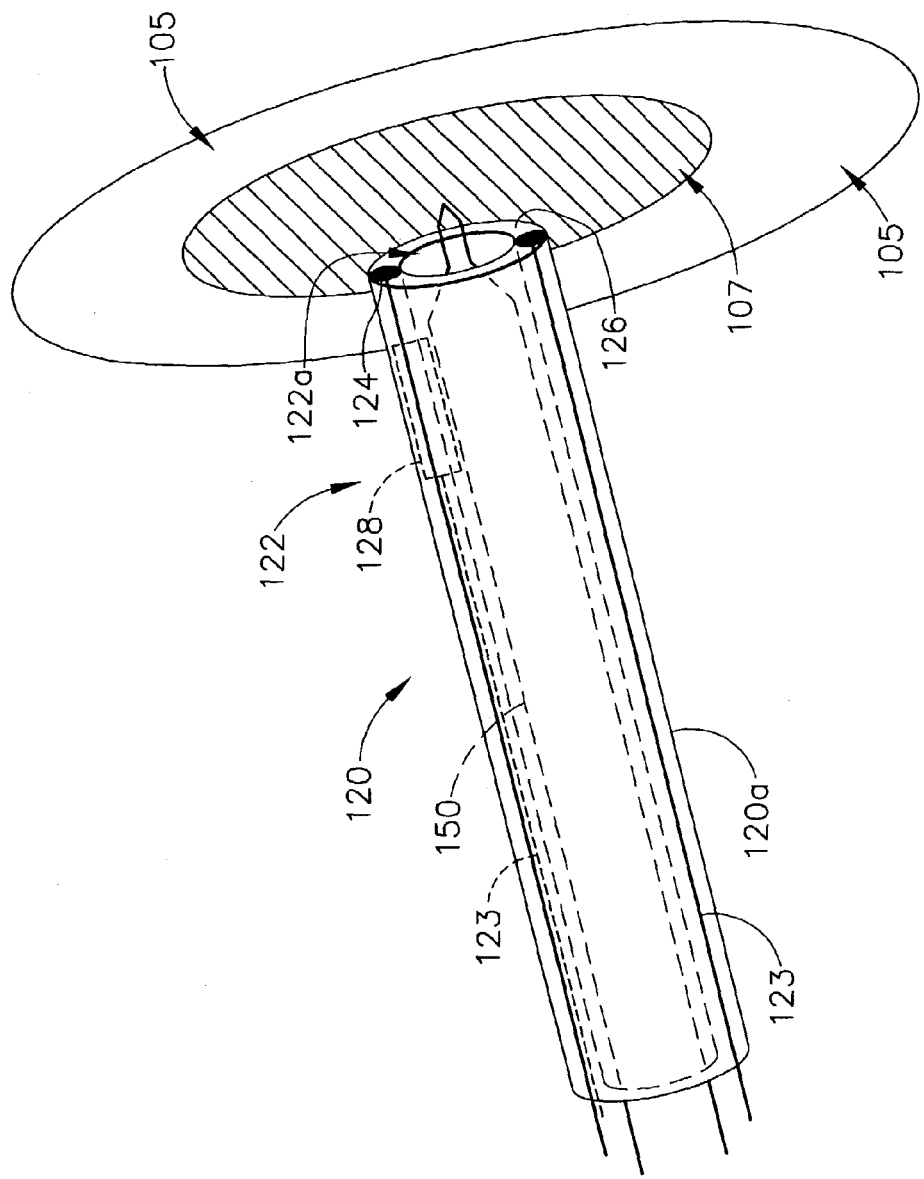
FIG. 13B is a schematic illustration of the sheath having a position sensor and at least one electrode and a penetrating device therein in accordance with the present invention being used to penetrate the fossa ovalis in the method of FIG. 13A accordance with the present invention.

FIGS. 13A and 13B illustrate an alternative embodiment of the method in accordance with the present invention. The method of the present invention depicted in FIGS. 13A and 13B is also directed toward a procedure involving the septum 105 and the fossa ovalis 107 such as a transseptal facilitation procedure. This alternative embodiment of the method in accordance with the present invention is similar to the transseptal facilitation method depicted in FIGS. 12A and 12B and as described above, i.e. both the method embodiment of FIGS. 12A and 12B and the method embodiment of FIGS. 13A and 13B are substantially similar with the exception of the use of the location sensor 128 within the sheath body 120*a* for the sheath 120 associated with the method embodiment of FIGS. 13A and 13B.

Accordingly, the method in accordance with the present invention depicted in FIGS. 13A and 13B is a navigated transseptal facilitation procedure utilizing the location sensor 128 located proximal of the distal tip electrode arrangement recording electrode segments 124*a* for guided movement (electromagnetic field guidance or navigation) of the distal end 122 of the sheath 120 to the septum 105 of the heart 100 (FIG. 1) as well as guidance of the distal tip 126 and distal tip electrode arrangement, i.e. recording electrode segments 124*a* against and across the tissue of the septum 105 and the fossa ovalis 107. Since the location sensor 128 generates signals for determining the location coordinates of the distal end 122 of the sheath 120, i.e. position coordinates and orientation coordinates, the sheath 120 can be guided and navigated to the heart 100 and within the heart 100 using only the location system 118 (FIGS. 2 and 3), i.e. without an imaging modality such as those mentioned previously. Thus, the method of navigated transseptal facilitation depicted in FIGS. 13A and 13B does not necessarily require an imaging modality such as fluoroscopy or any of the others mentioned above. Thus, the physician 151 (FIG. 3) can rely on the location information provided from the location sensor 128 in lieu of these imaging modalities. However, the sheath 120 having location sensor 128 as shown in FIGS. 13A and 13B can be utilized with any desired imaging modality such as fluoroscopy if the physician 151 so desires even through it is not a requirement in accordance with this embodiment of the method of the present invention.

When using the location sensor 128 on the distal end 122 of the sheath 120, the distal end 122 of the sheath 120 is navigated to the septal wall 105 using the location sensor 128. Additionally, as described in detail above (with respect to the method embodiment depicted in FIGS. 12A and 12B), the fossa ovalis 107 is identified in the septal wall 105 using the recording electrode segments 124*a* and the injury pattern detection techniques described in detail above.

Moreover, as mentioned above, the fossa ovalis 107 is identified as an area on the septal wall 105 that exhibits an injury pattern that is less of an injury pattern or even no injury pattern at all when compared to the injury pattern exhibited by other areas on the septal wall 105, i.e. for instance, the muscular areas of the septal wall 105 such as those areas outside of the fossa ovalis 107.

The only differences between the method embodiment of FIGS. 13A and 13B when compared to the method embodiment of FIGS. 12A and 12B, is the addition of the location sensor 128 on the sheath 120 as well as the ability to forego use of an imaging modality such as fluoroscopy, which has been replaced with the electromagnetic navigation abilities afforded by the location sensor 128 and location system 118 (FIG. 2).

Furthermore, the transseptal facilitation method embodiments described in FIGS. 12A, 12B, 13A and 13B respectively can be conducted with any of the guiding sheath 120 embodiments of the present invention such as those depicted in FIGS. 5, 6A, 6B, 7, 8, 9 and 10. Thus, the tissue characteristic or injury pattern recording techniques described in these method embodiments is not limited to a distal tip electrode arrangement having two recording electrode segments 124*a*, but also include distal tip recording electrode arrangements using a single distal tip electrode 124 such as a circumferentially arranged distal tip recording electrode 124 as shown in FIGS. 5, 6A and 6B respectively as well as the semi-circular distal tip recording electrode arrangement (four recording electrode segments 124*b*) shown in FIGS. 9 and 10.

Although the sheath embodiment of FIG. 6A of the present invention is schematically illustrated in the method embodiment of FIGS. 12A and 12B and the sheath embodiment of FIG. 8 is schematically depicted in the method embodiment of FIGS. 13A and 13B, these alternative embodiments for the methods in accordance with the present invention, such as a transseptal facilitation procedure, are not limited to these particular sheath embodiments (i.e. the hemi-circular split tip recording electrode arrangement).

Another alternative embodiment of the sheath 120 in accordance with the present invention is illustrated in FIGS. 4A and 4B respectively. In this sheath embodiment in accordance with the present invention, the sheath 120 has a distal end 122 without any type of recording electrode arrangement. But rather, a location sensor 128 alone is located at the distal end 122. As described above, the location sensor 128 permits the sheath 120 to be navigated within the patient's body 90 to any desired location within the body 90 such as a particular tissue site. Since the particular configuration, features and function of the location sensor 128 and the location system 118 (FIG. 2) has been described in great detail above, novel methods utilizing the sheath embodiment of FIGS. 4A and 4B will now be addressed.

Figure 11A:
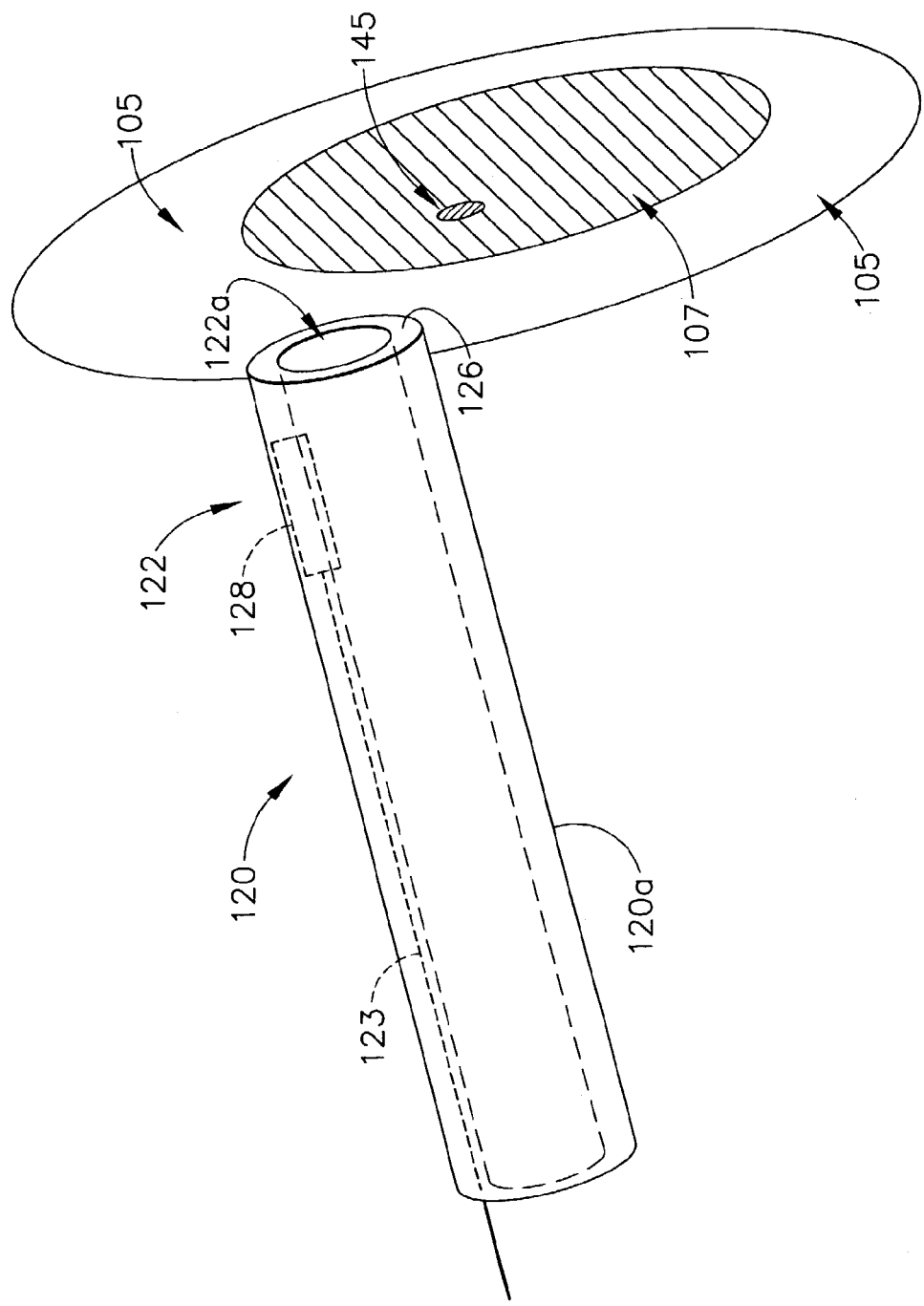
FIG. 11A is a schematic illustration of a guiding sheath having a position sensor in accordance with the present invention being used to identify the fossa ovalis in a method in accordance with the present invention.
Figure 11B:
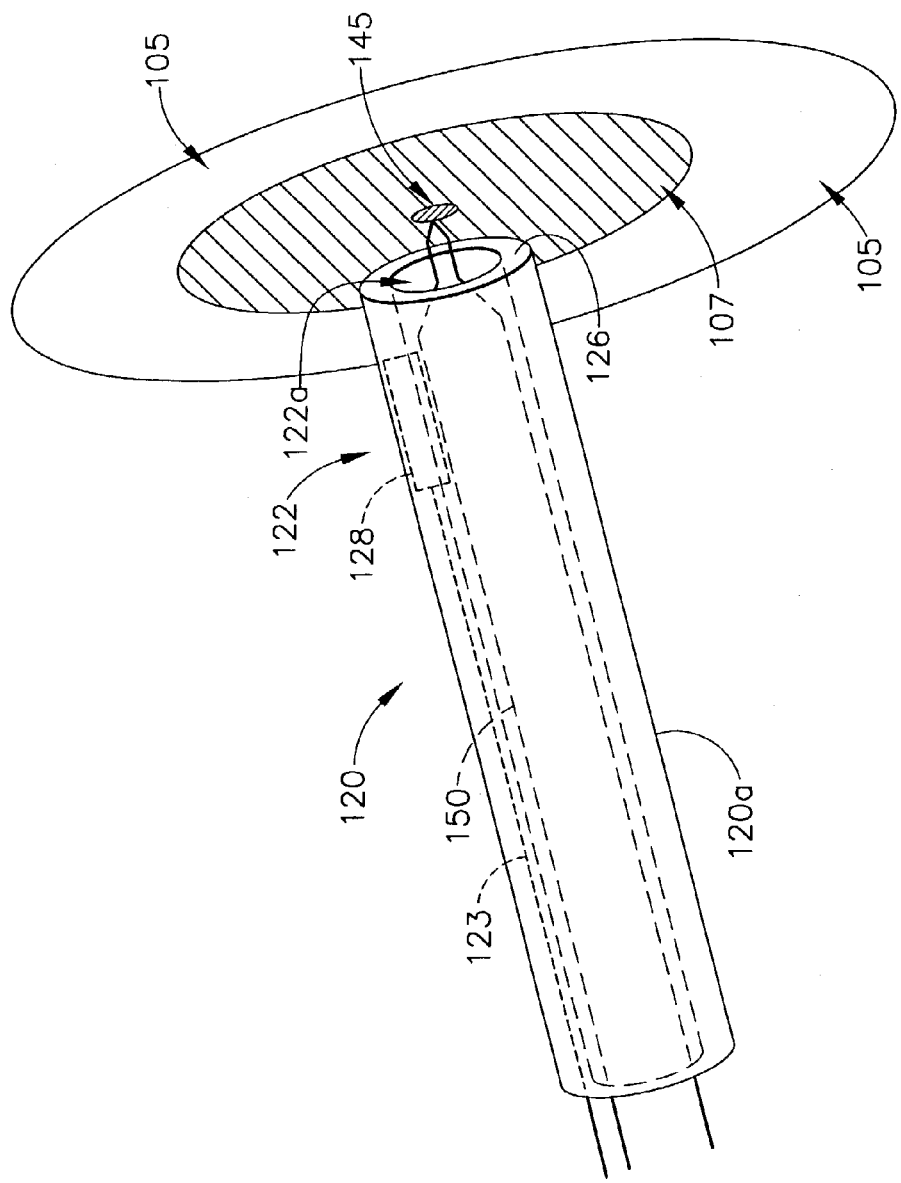
FIG. 11B is a schematic illustration of the sheath having a position sensor and a penetrating device therein in accordance with the present invention being used to penetrate the fossa ovalis in the method of FIG. 11A in accordance with the present invention.

Accordingly, one method utilizing the sheath embodiment 120 depicted in FIGS. 4A and 4B is directed toward identifying a tissue site such as the fossa ovalis 107 on the septal wall 105 and is associated with a transseptal facilitation procedure. FIGS. 11A and 11B illustrate the sheath 120 embodiment of FIGS. 4A and 4B wherein an optimal puncture site 145 (also referred to as a tag site) is achieved through various available methods. This includes identifying both the septal wall of the heart, to include muscular areas on the septal wall 105 of the heart 100, as well as the thin, fibrous membrane-like areas of the fossa ovalis 107. These tissue identification methods include using such modalities as fluoroscopy imaging that can be utilized with electrode catheters positioned in the right atrial appendage of the right atrium 115, the His bundle region and coronary sinus which all can be used as anatomical landmarks, and geography, for instance right atrium 115 and angiography, or ultrasound visualization such as through transesophageal echocardiography (TEE) or intracardiac echocardiography (ICE). Upon identifying the fossa ovalis 107 in the septal wall 105, a point is tagged 145 (tagged puncture site) at the fossa ovalis 107. The tagged puncture site 145 can be a particular location coordinate (identified by position and orientation coordinates) determined by using the location sensor 128 or the tagged puncture site 145 can also be a physical tag such as an active tag or a passive tag placed in the tissue at this site. Examples of active tags and passive tags that can serve as the tagged puncture site 145 (tagged point 145) are described in detail in U.S. Pat. No. 6,332,089; U.S. patent application Ser. No. 09/265,715 filed Mar. 11, 1999; U.S. patent application Ser. No. 10/029,595 filed Dec. 21, 2001; and U.S. patent application Ser. No. 10/173,197 filed Jun. 17, 2002, the disclosures this patent and these applications are incorporated by reference herein.

The tagged puncture site or tagged point 145 in the fossa ovalis 107 can be identified using various imaging modalities or imaging devices include fluoroscopy imaging devices, angiography imaging devices, ultrasound imaging devices to include ultrasound imaging devices such as those based on transesophageal echocardiography or intracardiac echocargiography. Additionally, the tagged puncture site 145 or tagged point 145 can be identified by using anatomical landmarks such as those mentioned above.

Additionally, the tagged puncture site 145 or tagged point 145 in the fossa ovalis 107 can be identified using electroanatomical mapping using the location system 118 (FIG. 2) along with it's surface reconstruction software which has been described in detail above. When using the location system 118 in an electroanatomical mapping procedure, the tagged point 145 is displayed on an electrical anatomical map on the display 145 of the system 118 as shown in FIG. 2.

After identifying the tagged point 145, either through utilizing specific location coordinates determined by using the location system 118 or a physical tag (an active tag or a passive tag such as those mentioned above), the sheath 120 is guided and navigated to the tagged point 145 of the fossa ovalis 107 using the location sensor 128.

As best illustrated in FIG. 11B, a penetrating device 150 is inserted into the lumen 122a of the body 120a of the sheath 120 and is extended out of the distal end opening at the distal end 126 of the body 120a such that the penetrating member 150 punctures the fossa ovalis 107 at the tagged point 145 (tagged puncture site 145) thereby creating an aperture in the fossa ovalis 107 leading to the chamber of the left atrium 110. Again, additional steps associated with transseptal facilitation procedures such as those steps described above include withdrawing the penetrating device 150 from the lumen 122a of the sheath 120 and providing another type of secondary device (either a diagnostic or therapeutic device) shaped to fit within the lumen 122a (working channel) of the sheath 120. Accordingly, these secondary devices can be used to perform either diagnostic procedures and/or therapeutic procedures in the left atrium 110 of the heart 100 after successful penetration of the fossa ovalis 107, i.e. at the tagged site 145.

Furthermore, all guiding sheath embodiments 120 shown in FIGS. 4A, 4B, 5, 6A, 6B, 7, 8, 9 and 10 respectively can be utilized either with a guide wire (not shown) or without a guide wire using the various guidance and navigation techniques previously described.

It will be appreciated that the preferred embodiments described above are cited by way of example and the full scope of the invention is limited only by the claims which follow.

What is claimed is:

1. A method for performing a procedure at a fossa ovalis in a septal wall of a heart, the method comprising the steps of:
    providing a sheath comprising a body, the body having a lumen extending therethrough and an open end at a distal end of the body, the body also having at least one electrode and a position sensor at the distal end of the body, the position sensor generating signals indicative of a location of the distal end of the body;
    navigating the sheath to the septal wall using the position sensor;
    reconstructing an electroanatomical map using the at least one electrode and the position sensor of the sheath;
    identifying the fossa ovalis in the septal wall using the at least one electrode and the position sensor of the sheath; and
    displaying the fossa ovalis as a tagged point on the map.

2. The method according to claim 1, further comprising identifying the fossa ovalis based on injury patterns detected using the at least one electrode.

3. The method according to claim 2, further comprising identifying the fossa ovalis by determing an injury pattern for an area on the septal wall that exhibits less of an injury pattern than injury patterns exhibited by other areas on the septal wall.

4. The method according to claim 3, further comprising detecting injury patterns using injury curves.

5. The method according to claim 4, further comprising detecting injury patterns with an electrocardiogram.

6. The method according to claim 5, further comprising displaying the injury patterns in the form of PQRST waves.

7. The method according to claim 2, further comprising identifying the fossa ovalis by finding an area on the septal wall that does not exhibit an injury pattern.

8. The method according to claim 1, further comprising determining the location coordinates of the tagged point using the position sensor.

9. The method according to claim 8, further comprising determining the location coordinates of the tagged point by identifying position coordinates of the point.

10. The method according to claim 9, further comprising identifying orientation coordinates for the tagged point.

11. The method according to claim 1, further comprising tagging the point at the fossa ovalis with a physical tag.

12. The method according to claim 11, further comprising tagging the point at the fossa ovalis using an active tag.

13. The method according to claim 11, further comprising tagging the point at the fossa ovalis using a passive tag.

14. The method according to claim 1, further comprising perforating the fossa ovalis.

15. The method according to claim 14, further comprising perforating the fossa ovalis by extending a penetrating device through the lumen and the distal end of the sheath.

16. The method according to claim 15, further comprising withdrawing the penetrating device from the sheath.

17. The method according to claim 16, further comprising extending a secondary device through the sheath and the fossa ovalis and into the left atrium of the heart.

18. The method according to claim 17, further comprising performing a diagnostic procedure in the left atrium with the secondary device.

19. The method according to claim 17, further comprising performing a therapeutic procedure in the left atrium with the secondary device.

* * * * *